United States Patent [19]
Abergel et al.

[11] Patent Number: 5,817,090
[45] Date of Patent: Oct. 6, 1998

[54] LASER DERMAL IMPLANTS FOR THE TREATMENT OF FACIAL SKIN DEPRESSIONS

[75] Inventors: Robert Patrick Abergel, Pacific Palisades, Calif.; Michael Slatkine, Herziiah, Israel; Douglass Mead, Allendale, N.J.; Eliezer Zair, Bney Brack, Israel

[73] Assignee: Laser Industries, Ltd., Tel Aviv, Israel

[21] Appl. No.: 979,077

[22] Filed: Nov. 26, 1997

Related U.S. Application Data

[63] Continuation of Ser. No. 383,724, Feb. 3, 1995, abandoned.

[51] Int. Cl.$^6$ .................................................. A61B 17/36
[52] U.S. Cl. ...................................................................... 606/9
[58] Field of Search ........................... 606/9, 10, 11, 606/12, 15, 16, 17; 607/89; 128/898

[56] References Cited

U.S. PATENT DOCUMENTS

| | | | |
|---|---|---|---|
| 3,884,236 | 5/1975 | Krasnov | 128/303 |
| 4,469,098 | 9/1984 | Davi. | |
| 4,566,453 | 1/1986 | Kumano et al.. | |
| 4,587,396 | 5/1986 | Rubin | 219/121 LU |
| 4,672,969 | 6/1987 | Dew | 128/397 |
| 4,733,660 | 3/1988 | Itzkan. | |
| 4,917,083 | 4/1990 | Harrington et al. | 606/15 |
| 5,071,417 | 12/1991 | Sinofsky | 606/8 |
| 5,280,378 | 1/1994 | Lombardo. | |
| 5,360,447 | 11/1994 | Koop | 606/9 X |
| 5,411,502 | 5/1995 | Zair | 606/10 |
| 5,522,813 | 6/1996 | Trelles | 606/9 X |
| 5,554,153 | 9/1996 | Costello et al. | 606/9 |
| 5,558,666 | 9/1996 | Dewey et al. | 606/10 X |

OTHER PUBLICATIONS

Sharplan Lasers, Inc. "Silk Touch Transformation" brochure, published in the United States in Jan. 1995, 4 pages.
Sharplan Lasers, Inc. "Advanced Technology for Aesthetic $CO_2$ Laser Surgery" brochure, published in the United States in Jan. 1995, 2 pages.
Sharplan Lasers, Inc. "Sharplan 771 Microscan" brochure, published in the United States in Jan. 1995, 3 pages.
Sharplan Lasers, Inc. "Sharplan 775" brochure, published in the United States in Jan. 1995, 2 pages.
Sharplan Lasers, Inc. "Sharplan 775/776/777 Microscan" brochure, published in the United States in Jan. 1995, 2 pages.
Sharplan Lasers, Inc. "Sharplan 771 General System Description" brochure, published in the United States in Jan. 1995, 17 pages.
Sharplan Lasers, Inc. "Sharplan 775A/B System Description" brochure, published in the United States in Jan. 1995, 23 pages.
Michael Slatkine, PhD, Yosef P. Krespi, MD; *Instrumentation for Office Laser Surgery;* Operative Techniques in Otolaryngology–Head and Neck Surgery, vol. 5, No. 4, Dec. 1994, pp. 211–217.
Aesthetic $CO_2$ Laser System literature, Aug. 1994; 2 pages.
R. Rox Anderson and John A. Parrish; *Selective Photothermolysis: Precise Microsurgery by Selective Absorption of Pulsed Radiation;* American Association for the Advancement of Science, 29 Apr. 1983, vol. 220, pp. 524–527.
Andrew Blitzer, MD, DDS, *Laser Photocoagulation in the Care of Patients with Osler–Weber–Rendu Disease* Operative Techniques in Otolaryngology–Head and Neck Surgery, vol. 5, No. 4, Dec. 1994, pp. 274–277.
Arielle Kauvar, M.D., *Laser Therapy for Cutaneous Vascular Lesions,* Operative Techniques in Otolaryngology–Head and Neck Surgery, vol. 5, No. 4, Dec. 1994, pp. 250–258.

*Primary Examiner*—Jennifer Bahr
*Assistant Examiner*—Sonya Harris-Ogugua
*Attorney, Agent, or Firm*—Cobrin Gittes & Samuel

[57] ABSTRACT

A method of treating facial skin depressions is provided in which, following laser ablation of the epidermal layer, the underlying dermal plug of skin is obtained having minimal thermal damage and is implanted into an area of depressed skin.

12 Claims, 1 Drawing Sheet

LASER DERMAL IMPLANTS FOR THE TREATMENT OF FACIAL SKIN DEPRESSIONS

This is a continuation of application Ser. No. 08/383,724 filed Feb. 3, 1995 now abandoned.

BACKGROUND

The present invention relates to a method of obtaining and implanting dermal grafts beneath facial skin depressions in which the donor dermal layer is removed and subsequently implanted under the facial depression.

Dermal and subdermal "fillers" have been used for many years to attempt correction of acne scar depressions and rhytides. Silicone, popular for many years, has potentially serious side effects such as silicone granuloma. While injectable collagen is readily available, easy to administrate and is generally effective in correcting small defects, the need for repeat treatment and the risk of allergic reactions is a drawback for many patients. Autologous fat transplantation is unpredictable due to the lack of survival of or cellular damage to the fat cells which may occur during harvesting.

Dermal grafts have been used for correction of cutaneous depressions where the epidermis is removed by dermabrasion. This method, however, is imprecise by nature and likely to damage the underlying dermis. Failed attempts to use human tissue demonstrate the importance of ensuring the integrity of the transplant.

SUMMARY OF THE INVENTION

The present invention provides a method of treating skin depressions by ablating material of living epidermal skin with a laser beam of light such that an underlying dermal layer of skin is exposed; obtaining at least a portion of the dermal layer of skin; and implanting the dermal plug in an area of living skin in need of treatment. The epidermal skin is irradiated with a laser beam of light such that the material is ablated. A carbon dioxide laser may be used.

The method of the present invention further comprises passing a laser beam of light through a reflector system and moving the beam of light in a predetermined pattern on the material of living epidermal skin tissue such that elements of the material are irradiated sequentially and continuously, thereby creating ablation that is uniform but only to a predetermined depth. The predetermined pattern may be Lissajous figures or a spiral pattern. The reflector system comprises two reflecting surfaces such as mirrors or prisms.

It is an objective of the present invention to provide a method of treating facial skin depressions.

It is an objective of the present invention to provide a method of preparing dermal implants for the treatment of facial skin depressions which maintain the full integrity of the dermis.

It is a further objective of the present invention to provide a laser method of obtaining dermal implants for the treatment of facial skin depressions in which the dermal implant is substantially unimpaired by thermal damage.

DETAILED DESCRIPTION OF THE INVENTION

Figure 1:
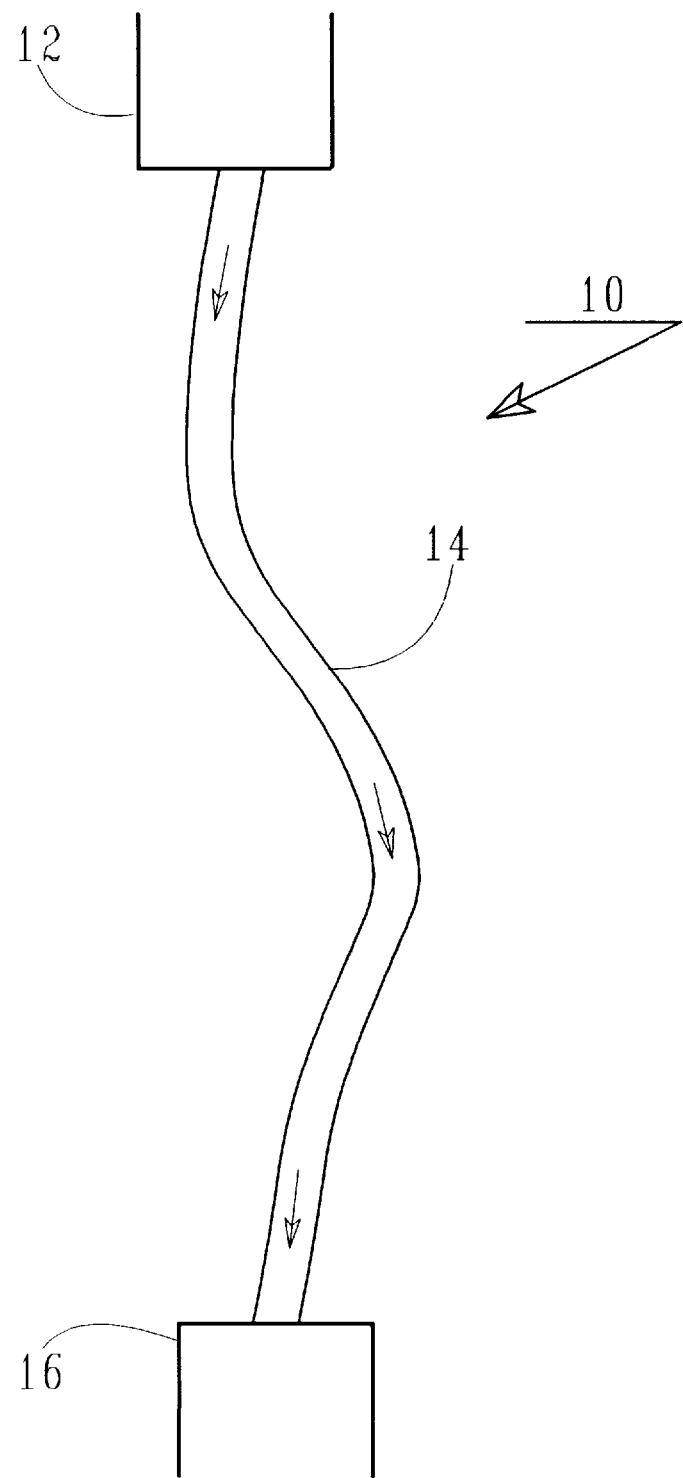
FIG. 1 depicts a fiber through which a laser beam may be emitted.

The present invention utilizes a laser for irradiating the epidermal layer of skin to access the dermal layer with minimal thermal damage thereto. A portion of the dermal layer is then obtained for implantation in areas of facial skin depressions. Carbon dioxide lasers may be used which are pulsed or C.W.

In the present invention a laser is preferably used in conjunction with a flash scanner system. Flash scanner systems are described in U.S. patent application Ser. No. 08/175,980 entitled "A System for Causing Ablation of Irradiated Material of Living Tissue While Not Causing Damage Below a Predetermined Depth" which has been allowed at this writing, and in the U.S. patent application filed on Dec. 19, 1994 entitled "Method and Apparatus for Applying Laser Beam to a Working Surface, Particularly for Ablating Tissue" (no U.S. Ser. No. issued as yet). The flash scanner system contains reflectors such as mirrors or prisms which are angularly positioned to deflect the laser beam and irradiate in a predetermined pattern. The movements of the reflectors of the flash scanner are generally microprocessor controlled. The carbon dioxide laser is the laser of choice in conjunction with the flash scanner for the uniform ablation of irradiated material. The laser beam of light may be emitted through an articulated arm or, as provided herein, a laser fiber. A focused or slightly defocused beam may be used. The use of a laser with the flash scanner permits all irradiated skin to be ablated with negligible thermal damage and char to the underlying skin. Moreover, any residual thermal damage is shallow and controlled.

The flash scanning technique permits vaporization of the epidermal layer with minimal thermal damage to the underlying dermal layer. The treatment can be performed using a predetermined pattern of a spiral or Lissajous figures. A spiral pattern is preferable for skin resurfacing as homogenous vaporization is particularly desirable for cosmetic or aesthetic surgeries.

Preferably, the beam travels through an optical waveguide before reaching the flash scanner. FIG. 1 depicts such an optical waveguide 10 through which a laser beam may travel. The laser beam is generated at laser source 12 and travels through the optical waveguide 14 in the direction of the arrows to the flash scanner 16 containing the reflector system. The optical waveguide, which is loosely referred to as a fiber, provides superior waveguide capability for the laser beam. It also participates in defocusing the laser beam. After passing through the flash scanner, the laser beam is emitted to irradiate the skin surface (not shown here).

At least a portion of the papillary dermal layer accessed by the ablation of the overlying epidermal layer is then harvested and implanted under the depressed skin in need of treatment by known methods such as punch biopsy or by harvesting dermal strips for use of commercially available equipment.

It has been recognized that dermal implants harvested following laser ablation of the epidermal layer as provided herein retain the integrity of the dermal layer and provides the fibroblasts and connective tissue with a better chance of survival.

EXAMPLE

Preparation of the Laser Dermal Plug

After obtaining an informed consent, the patient lying in the decubitus position is prepped in a sterile fashion. The donor site is selected either on the retroauricular area or on the inner aspect of the arm, adjacent to the axilla. The donor site is anesthetized locally by subdermal injection of a preparation containing Xylocaine 1%, Epinephrine 1:100:000, and Sodium Bicarbonate.

Selective Laser Removal of the Epidermis at the Donor Site

A continuous wave $CO_2$ laser was used to selectively ablate the epidermis in a spiral pattern at a power of 7 watts, 0.2 sec exposure. The laser is connected to the reflecting system with a 125 mm focussing handpiece, which produces a 150 micron focal spot. For the preparation of the laser dermal implant a homogenous 3 mm diameter area was chosen to be scanned.

Flash scanning with a focused beam spot size as small as 150 microns permits the attainment of char free ablation with very high densities on tissue even at a low power level. An estimate of how thin the single tissue layer can be vaporized is obtained by realizing that the total energy delivered to the tissue in a single 0.2 sec pulse at 7 W operating laser power level is 1400 mj. This can be extended to up to 4000 mj with a 6 m scanning diameter handpiece. Since the thermal energy necessary to ablate 1 mm$^3$ of tissue is about 3000 mj/mm$^3$, the single layer vaporization depth produced at 7 W, 0.2 sec laser parameters is 50 to 100 microns.

The $CO_2$ laser wavelength of 10.6 microns is absorbed by water and will not penetrate the dermis at the power used is the study. The 150 micron spot was programmed to linger at any given point for less than 1 millisecond, the thermal relaxation time required for heat generated by the laser for diffusion from the epidermis to the dermis. Therefore, a selective epidermal ablation was performed without damaging the underlying dermis as confirmed by histology. The histology showed an underlying residual thermal necrosis depth of 100 microns.

Harvest of the Laser Dermal Plug

The dermal implants were then harvested using either punch biopsy of size varying from 2–4 mm to be used for depressed scars or through punching a strip to obtain skin strips for correction of naso-labial fold or lip augmentation. Strips of dermis may be harvested of of various lengths and thickness according to the desired correction. The dermal grafts are then excised from the subcutaneous fat and emersed in a solution of sterile saline, awaiting implantation.

Implantation of Laser Dermal Plug

The skin was prepped in a sterile fashion and the depressions were designated with a surgical marking pen. The size of the depression was assessed carefully to determine the size of the dermal graft. After local anesthesia, a puncture was then made at the periphery of the scar tangentially at a 45° angle from the surface of the skin. A small subdermal tunnel was then created under the depression using a blunt Tunneling Rod™ instrument. The laser dermal plug was then inserted within the cavity with a serrated Iris forceps. A sterile guaze was then applied over liquid adhesive for closure of the original puncture. The minimal trauma inflicted to the skin by the puncture healed quickly without scars, permitting the patient to return to work the following day after the procedure.

Implantation of the Laser Dermal Implant Plug for Lip Augmentation

After photographs, the skin was prepped in a sterile fashion and the vermillion border was designated with a surgical marking pen. The lips were anethetised using a nerve block. A bloodless puncture was performed using an 80 mm handpiece mounted on the reflector system. The puncture was made at the labial commissure and a blunt tunnel undermined using a specifically designed Tunneling Rod™ instrument. The dermal implant was then gently inserted. After positioning of the grafts, the puncture was closed by a 6.0 nylon suture left in place for 24 hours. Fast recovery was achieved with the patient returning to work the next day.

Implantation of the Laser Dermal Plug for the Correction of the Naso-Labial Folds The skin was prepared in a sterile fashion and the recipient site was outlined. A small puncture was made at the bottom part of the naso-labial fold. After undermining with the Tunneling Rod™ instrument, the dermal plugs were inserted. The site was closed with a sterile guaze applied over liquid adhesive.

What is claimed is:

1. A method of treating a depression in the skin of a mammal, comprising the steps of:

making a puncture at one side of the depression;

inserting a tunneling tool through the puncture so as to hollow a space under the depression;

selecting a donor site on the skin of the mammal at a remove from the depression;

applying a laser beam for ablating the epidermal layer of the skin at the donor site, thereby exposing dermis at the donor site;

harvesting a plug of the dermis at the donor site; and inserting the plug into the space under the depression.

2. The method of claim 1, additionally comprising:

providing a carbon dioxide laser for applying said laser beam.

3. The method of claim 2, wherein said step of applying said laser beam further comprises passing said laser beam through an optical waveguide to defocus said laser beam prior to ablating said epidermal layer.

4. The method of claim 1, wherein said step of applying said laser beam further comprises passing said laser beam through an optical waveguide to defocus said laser beam prior to ablating said epidermal layer.

5. The method of claim 1, wherein the step of applying said laser beam additionally comprises scanning said laser beam with a flash scanner system to provide a predetermined spiral pattern on said epidermal layer.

6. The method of claim 5, additionally comprising passing said laser beam through an optical waveguide to defocus said laser beam prior to ablating said epidermal layer.

7. The method of claim 5, wherein the scanning step includes ensuring less than a 1 millisecond exposure time of said laser beam to each individual site within the predetermined spiral pattern on said epidermal layer.

8. The method of claim 1, wherein the step of applying said laser beam additionally comprises scanning said laser beam with a flash scanner system to provide a predetermined Lissajous pattern on said epidermal layer.

9. The method of claim 8, further comprising passing said laser beam through an optical waveguide to defocus said laser beam prior to ablating said epidermal layer.

10. The method of claim 8, wherein the scanning step includes ensuring less than a 1 millisecond exposure time of said laser beam to each individual site within the predetermined Lissajous pattern on said epidermal layer.

11. The method of claim 1, wherein the step of applying said laser beam additionally comprises emitting a continuous wave $CO_2$ beam as said laser beam.

12. A method for preparing a dermal implant comprising:

in a first step applying a laser beam to an area of skin to ablate only a portion of the epidermal tissue layer of said area of said skin, and to expose a portion of the dermal tissue layer of said skin, said dermal tissue layer being substantially free of thermal damage; and in a second step removing a volume of dermal tissue from said exposed dermal tissue layer.

* * * * *